United States Patent [19]

Berman et al.

[11] Patent Number: 4,677,219

[45] Date of Patent: Jun. 30, 1987

[54] SUBSTITUTED BENZONITRILES

[75] Inventors: Ellen M. Berman; Mark J. Suto, both of Ann Arbor, Mich.

[73] Assignee: Warner-Lambert Company, Morris Plains, N.J.

[21] Appl. No.: 886,463

[22] Filed: Jul. 17, 1986

[51] Int. Cl.[4] .................. C07C 121/54; C07C 121/52
[52] U.S. Cl. .................. 558/419; 544/291; 558/418; 558/423
[58] Field of Search .............. 544/291; 558/418, 419, 558/423

[56] References Cited

FOREIGN PATENT DOCUMENTS 1345502 1/1974 United Kingdom .

OTHER PUBLICATIONS

Elslager et al., "Chemical Abstracts", vol. 80, 1974, col. 48026s.
Elslager et al., "Chemical Abstracts", vol. 89, 1978, col. 89: 157152m.
Kienzle, "Chemical Abstracts", vol. 99, 1983, col. 99: 38484t.
McCullough et al., "Chemical Abstracts", vol. 87, 1977, col. 87: 95483t.
E. F. Elslager et al., J. Med. Chem., 26: 1753–1760 (1963).
W. L. F. Amarego, "Fused Pyrimidines–Part I, Quinazolines," Wiley Interscience, New York, 1967, pp. 330–332.
J. Davoll et al, J. Chem. Soc., Section C, (1970) 997–1002.

Primary Examiner—Glennon H. Hollrah
Assistant Examiner—James H. Turnipseed
Attorney, Agent, or Firm—Jerry F. Janssen

[57] ABSTRACT

An improved process for the preparation of 6-substituted-5-alkyl-2,4-quinazolinediamines, useful in the production of trimetrexate and similar antifolate agents, together with several novel intermediates are disclosed.

4 Claims, No Drawings

SUBSTITUTED BENZONITRILES

BACKGROUND OF THE INVENTION

The present invention is related to chemical processes and intermediates. More particularly, it is concerned with certain novel 5,6-substituted-2,4-quinazolinediamines and an improved process for preparing the compounds.

The compound 5-methyl-6-[[(3,4,5-trimethoxyphenyl)amino]methyl]-2,4-quinazolinediamine, known also by its trivial name timetrexate, is one of an important class of substituted 2,4-quinazolinediamines which are active folic acid antagonists possessing both antimalarial and anti-tumor activity. [See E. Elslager et al., *J. Med. Chem.*, 26: 1753–1760 (1983)].

These antifolate drugs are presently generally prepared by the reductive coupling of the appropriately substituted benzeneamine with the appropriately substituted 6-cyano-2,4-quinazolinediamine. The 2,4-diaminoquinazolines required for this process have usually been prepared by a lengthy process which involves amination of the corresponding 2,4-dichloroquinazolines or by reaction of substituted o-aminobenzonitriles with dicyandiamide or cyanamide. [W. L. F. Armarego, "The Chemistry of Heterocyclic Compounds, Fused Pyrimidine. Part I. Quinazolines," Interscience, New York, 1967, pp. 330–332.]

Neither of these routes, however, is useful for the preparation of the substituted 6-cyano-2,4-quinazolinediamines which are necessary for the preparation of trimetrexate and related antifolate drugs via the convenient reductive coupling method.

J. Davoll et al., *J. Chem. Soc.*, Section C, (1970) 997–1002 disclose a route for preparing the desired substituted 6-cyano-2,4-quinazolinediamines involving a multi-step synthesis which begins with the substituted 6-nitro-2,4-quinazolinediamines; proceeds through reduction to the substituted 2,4,6-triaminoquinazolines; and then through diazotization of the "aromatic" 6-amino-substituent and treatment with cuprous cyanide.

The various methods disclosed in the literature for preparing the substituted 6-cyano-2,4-quinazolinediamines required for the synthesis of trimetrexate and its analogues, require a large number of steps, with the attendant lower overall yields and increased cost. There has thus been a need for a process for the production of 5,6-substituted-2,4-quinazolinediamines which are useful in the production of trimetrexate and related antifolate compounds which overcomes these disadvantages.

SUMMARY OF THE INVENTION

In accordance with one aspect of the present invention, there is provided an improved process for preparing compounds of the formula

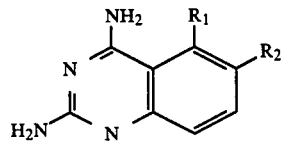

where $R_1$ is alkyl of from one to three carbon atoms and $R_2$ is bromine, chlorine, or cyano, comprising reacting a compound of the formula

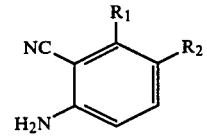

with chloroformamidine hydrochloride at a temperature of between 150° C. and 250° C., followed by isolation and purification of the product in the conventional manner.

In accordance with another aspect of the invention, there are provided novel intermediates for preparation of trimetrexate and analogous quinazolinediamine antifolates, said intermediates selected from the group 2-methyl-4-nitro-1,3-benzodinitrile; 4-amino-2-methyl-1,3-benzodinitrile; 6-amino-3-bromo-2-methylbenzonitrile; 6-amino-3-chloro-2-methyl-benzonitrile; 6-bromo-5-methyl-2,4-quinazolinediamine; and 6-chloro-5-methyl-2,4-quinazolinediamine.

DETAILED DESCRIPTION

The 6-cyano-2,4-quinazolinediamines or corresponding 6-aldehyde compounds which are required for the preparation of trimetrexate and analogous antifolates have been prepared in the past by the general methods outlined in Reaction Sequence 1.

The 5-substituted-6-nitro-2,4-quinazolinediamines, II, have been prepared by one of three methods: (a) nitration of the 5-substituted-2,4-quinazolinediamines; (b) reaction of 2-chloro-5-nitrobenzonitrile with guanidine carbonate; or (c) reaction of 5-nitro-2-aminobenzonitrile with guanidine. [J. Davoll et al., *J. Chem. Soc.*, Section C, (1970) 997–1002.]

The nitro-compounds, II, are then reduced, either by the action of tin chloride or catalytically by hydrogen, to the corresponding 5-substituted-2,4,6-triaminoquinazolines, III.

The triamines, III, are next diazotized by the action of nitrous acid, and reacted with copper (I) cyanide to produce the 5-substituted-6-cyano-2,4-quinazolinediamines, IV. The cyano-compounds, IV, are then converted to the antifolate compounds, V, by reductive coupling with the desired arylamine, VI.

The present invention eliminates a number of steps in this prior art process, including the undesirable diazotization step, by employing the process depicted in Reaction Sequence 2.

In the process of this invention, the 2-cyano-4-substituted-3-alkylbenzeneamines, VII, are reacted with chloroformamidine hydrochloride at a temperature of between about 150° C. to about 250° C., preferably between about 150° C. to about 175° C. to produce the 5-alkyl-6-substituted-2,4-quinazolinediamines, VIII. The reaction is allowed to proceed to completion, the time required being between about one-half to two hours.

REACTION SEQUENCE 1
(Prior Art)

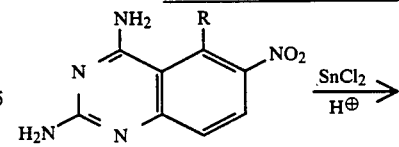

II

REACTION SEQUENCE 1 (Prior Art) -continued

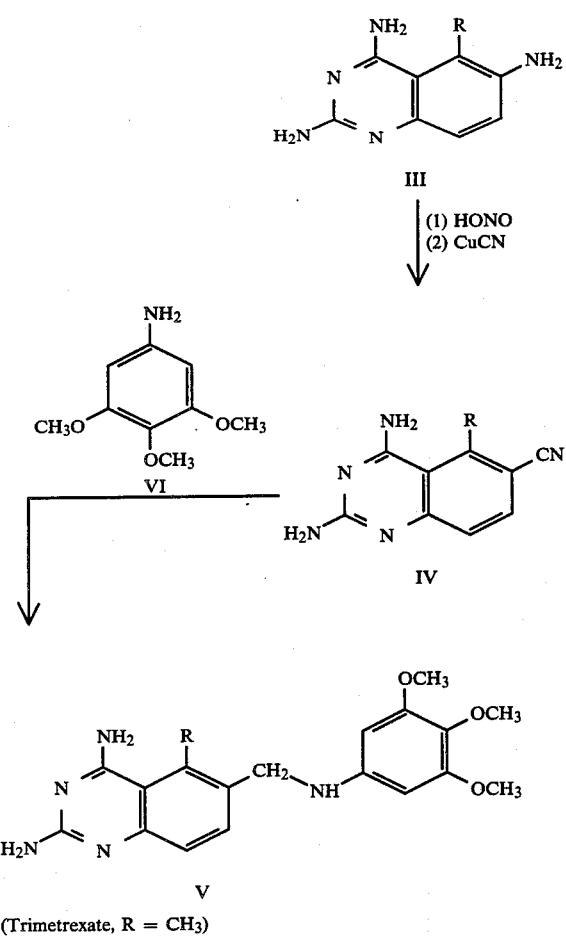

(Trimetrexate, R = CH₃)

REACTION SEQUENCE 2 (Present Invention)

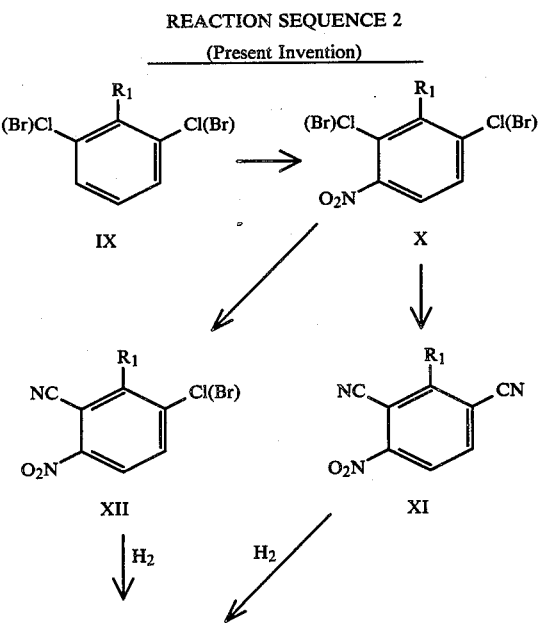

REACTION SEQUENCE 2 (Present Invention) -continued

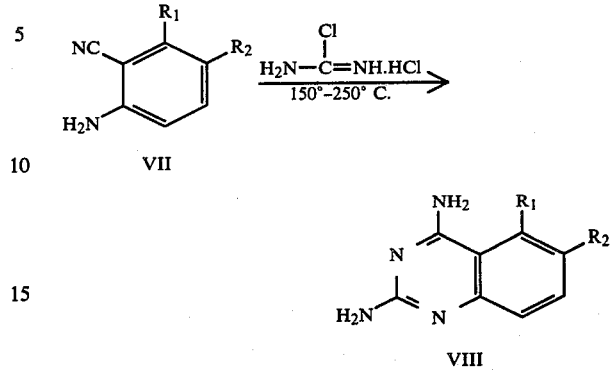

The cyclization reaction producing VIII is enhanced by the addition of a non-reactive polar solvent such as ethylene glycol dimethyl ether ("glyme"), bis-ethylene glycol dimethyl ether ("diglyme"), dimethyl sulfoxide, dimethylsulfone, and the like. Dimethyl sulfone is preferred because of its polarity and high boiling point.

The 5-alkyl-6-cyano-2,4-quinazolinediamines, VIII, are prepared, in accordance with the method of this invention, by starting with the known 2,6-dibromo- or 2,6-dichloro-alkylbenzenes, IX. The dihaloalkylbenzenes, IX, are nitrated in the conventional manner with concentrated nitric acid to produce the 2,6-dihalo-3-nitrotoluenes, X.

The dihalo-compounds, X, are converted by the action of copper (I) cyanide at temperatures of between about 150° C. to about 200° C. to the dicyano compounds, XI. This reaction is preferably carried out in the presence of a polar, non-reactive solvent such as N-methylpyrrolidone. Under milder conditions, the halomonocyano-compounds, XII, are produced.

The following illustrative examples are provided to enable one skilled in the art to practice the present invention, and are not to be read as limiting the scope of the invention as it is defined by the appended claims.

PREPARATION OF 2,6-DIBROMO-3-NITROTOLUENE

To 38 g of 2,6-dibromotoluene (0.152 mol) was added dropwise with stirring, over a period of thirty minutes, 76 ml of 70% nitric acid. An exothermic reaction was observed. The resulting mixture was stirred for an additional sixty minutes, after which time the mixture was poured into 1500 ml of ice water. The solids which separated were collected by filtration and dried to yield 44.62 g of 2,6-dibromo-3-nitrotoluene. Recrystallization of the reaction product from ethyl alcohol-water yielded material melting at 47°-48° C.

PREPARATION OF 2,6-DICYANO-3-NITROTOLUENE

A mixture of 2,6-dibromo-3-nitrotoluene (7 g, 23.7 mmol), copper (I) cyanide (5.14 g, 59.3 mmol), and 100 ml of N-methylpyrrolidone was heated to 180°-190° C. in an oil bath until the reaction was complete as indicated by thin-layer chromatographic monitoring of the progress of the reaction.

The resulting dark mixture was flash chromatographed over silica gel, eluting with 10% ethyl acetate/hexane, to yield 1.57 g of 2,6-dicyano-3-nitrotoluene, mp 122°–124° C.

Analyzed for $C_9H_5N_3O_2$: Calculated: C, 57.75%; H, 2.67%; N, 22.45%; Found: C, 57.68%, H, 2.79N, 22.43%.

PREPARATION OF 2,4-DICYANO-3-METHYLBENZENEAMINE

To a solution of 7.17 g of tin (II) chloride dihydrate in 7.2 ml of hydrochloric acid was added 18 ml of acetic acid followed by the dropwise addition of 1.9 g (10.1 mmol) of 2,6-dicyano-3-nitrotoluene in 18 ml of acetic acid.

The resulting solution was stirred at room temperature for thirty minutes, concentrated, and 75 ml of 2 molar aqueous sodium hydroxide solution was then added. This mixture was stirred overnight and the solids which separated were collected by filtration and extracted in a Soxhlet extractor with methyl alcohol.

The methanol was removed from the extract under vacuum, and the residue was flash chromatographed over silica gel, eluting with 10% methanol/chloroform. The product was recrystallized from ethanol/water to yield 0.56 g of 2,4-dicyano-3-methylbenzeneamine, mp 209°–210° C.

Analyzed for $C_9H17N_3$: Calculated: C, 68.77%; H, 4.48%; N, 26.73%; Found: C, 68.77%; H, 4.60%; N, 26.99%.

PREPARATION OF 2,4-DIAMINO-5-METHYL-6-QUINAZOLINECARBONITRILE

A mixture of 0.3 g (1.91 mmol) of 2,4-dicyano-3-methylaniline, 0.44 g (3.82 mmol) of chloroformamidine hydrochloride, and 0.7 g of dimethylsulfone was heated to 170°–175° C. The mixture solidified after a time, and was allowed to cool to room temperature. Water (20 ml) was added, and the resulting mixture was made basic with 1 molar aqueous sodium hydroxide solution, filtered, and washed with water. The solids were triturated with methanol to yield 0.167 g of 2,4-diamino-5-methyl-6-quinazolinecarbonitrile, mp>270° C. The infrared, mass, and proton magnetic resonance spectra corresponded to those of a known sample of the compound.

PREPARATION OF 3-BROMO-2-METHYL-6-NITROBENZONITRILE

To a mixture of 2,6-dibromo-3-nitrotoluene (1.0 g, 3.4 mmol) in 14 ml of N-methylpyrrolidinone was added 0.323 g of freshly prepared copper (I) cyanide. The reaction was stirred and heated at a temperature of 150° C. under a nitrogen atmosphere for a period of three hours. After this period, the reaction mixture was cooled to room temperature, diluted with dichloromethane, and washed with 10% aqueous sodium thiosulfate solution. The organic layer was separated, dried, and concentrated under vacuum to remove the solvent. The residue was chromatographed on silica gel, eluting with 20% ethyl acetate/80% hexane, to afford 0.293 g of 3-bromo-2-methyl-6-nitrobenzonitrile as a yellow-white crystalline solid, mp 116°–118° C.

Analyzed for $C_8H_5BrN_2O_2$: Calculated: C, 28.51%; H, 1.71%; N, 4.75%; Found: C, 28.43%; H, 1.85%; N, 4.95%.

PREPARATION OF 3-CHLORO-2-METHYL-6-NITROBENZONITRILE

The title compound was prepared using the method described above for preparing 3-bromo-2-methyl-6-nitrobenzonitrile, except that the reaction was carried out at 210° C. and employed 2,6-dichloro-3-nitrotoluene as the starting material. The infrared spectrum of a potassium bromide pellet of the product exhibited principal absorption peaks at 3121, 2231, 1602, 1560, 1530, and 1348 receiprocal centimeters.

The mass spectrum of the product exhibited peaks at m/e=198 (M+2), 196 (M), 166, 168, 123, and 125.

PREPARATION OF 6-BROMO-5-METHYL-2,4-QUINAZOLINEDIAMINE

A mixture of 0.23 g (1.09 mmol) of 6-amino-3-bromo-2-methylbenzonitrile, 0.25 g (2.19 mmol) of chloroformamidine hydrochloride, and 0.4 g of dimethylsulfone was heated in a bath at 175° C. The mixture solidified after a time, and was allowed to cool to room temperature. Water was added, and the resulting mixture was made basic with 1 molar aqueous sodium hydroxide solution, filtered, and washed with water. The solids were triturated with methanol to yield 0.19 g of 6-bromo-5-methyl-2,4-quinazolinediamine.

The infrared spectrum of a potassium bromide pellet of the product exhibited principal absorption peaks at 3437 and 1666 reciprocal centimeters.

The proton magnetic resonance spectrum of a hexadeutero-dimethylsulfoxide solution of the compound exhibited peaks at 2.81 (singlet, 3H); 6.15 (broad singlet, 2H); 6.96 (doublet, 1H), and 7.58 (doublet, 1H) parts per million downfield from tetramethylsilane.

Analyzed for $C_9H_9BrN_4$: Calculated: C, 42.71%; H, 3.58%; Br, 31.56%; N, 22.13%; Found: C, 42.72%; H, 3.51%; Br, 30.23%; N, 22.26%%.

PREPARATION OF 6-CHLORO-5-METHYL-2,4-QUINAZOLINEDIAMINE

A mixture of 0.89 g (5.11 mmol) of 6-amino-3-chloro-2-methylbenzonitrile, 1.17 g (10.2 mmol) of chloroformamidine hydrochloride, and 1.87 g of dimethylsulfone was heated in a bath at 175° C. The mixture solidified after a time, and was allowed to cool to room temperature. Water was added, and the resulting mixture was made basic with 1 molar aqueous sodium hydroxide solution, filtered, and washed with water. The solids were triturated with methanol to yield 0.97 g of 6-chloro-5-methyl-2,4-quinazolinediamine.

The infrared spectrum of a potassium bromide pellet of the product exhibited principal absorption peaks at 1667 and 1632 reciprocal centimeters.

The proton magnetic resonance spectrum of a hexadeutero-dimethylsulfoxide solution of the compound exhibited peaks at 2.75 (singlet, 3H); 6.20 (broad singlet, 2H); 7.08 (multiplet, 3H); and 7.51 (doublet, 1H) parts per million downfield from tetramethylsilane.

Analyzed for $C_9H_9ClN_4$: Calculated: C, 51.80%; H, 4.34%; Cl, 16.99%; N, 26.85%; Found: C, 51.40%; H, 4.52%; Cl, 17.01%; N, 27.07%%.

We claim:
1. The compound having the name 2-methyl-4-nitro-1,3-benzodinitrile.
2. The compound having the name 4-amino-2-methyl-1,3-benzodinitrile.
3. The compound having the name 6-amino-3-bromo-2-methylbenzodinitrile.
4. The compound having the name 6-amino-3-chloro-2-methylbenzonitrile.

* * * * *

UNITED STATES PATENT AND TRADEMARK OFFICE
CERTIFICATE OF CORRECTION

PATENT NO. : 4,677,219

DATED : June 30, 1987

INVENTOR(S) : Ellen M. Berman, et al

It is certified that error appears in the above-identified patent and that said Letters Patent is hereby corrected as shown below:

On the title page item [75] Inventors: should read

--Ellen M. Berman; Mark J. Suto; and H. D. Hollis, Showalter, all of Ann Arbor, Mich.--.

Signed and Sealed this

Fifth Day of May, 1992

Attest:

DOUGLAS B. COMER

*Attesting Officer*  *Acting Commissioner of Patents and Trademarks*

UNITED STATES PATENT AND TRADEMARK OFFICE
CERTIFICATE OF CORRECTION

PATENT NO. : 4,677,219

DATED : June 30, 1987

INVENTOR(S) : Ellen M. Berman, et al

It is certified that error appears in the above-identified patent and that said Letters Patent is hereby corrected as shown below:

On the title page item [75] Inventors: should read
-- Ellen M. Berman, Mark J. Suto; and H.D. Hollis Showalter,
all of Ann Arbor, Mich.--.

This certificate supersedes Certificate of Correction issued
May 5, 1992

Signed and Sealed this

Twenty-ninth Day of December, 1992

Attest:

DOUGLAS B. COMER

Attesting Officer

Acting Commissioner of Patents and Trademarks